(12) United States Patent
Barriskill et al.

(10) Patent No.: US 7,346,396 B2
(45) Date of Patent: Mar. 18, 2008

(54) INTERFACE TO FES CONTROL SYSTEM

(75) Inventors: Andrew Barriskill, Lane Cove (AU); Michael Robert Duncan, Lane Cove (AU); Simon Geoffrey Parker, Randwick (AU)

(73) Assignee: Neopraxis Pty Ltd, Lane Cove (AU)

( * ) Notice: Subject to any disclaimer, the term of this patent is extended or adjusted under 35 U.S.C. 154(b) by 492 days.

(21) Appl. No.: 10/344,554

(22) PCT Filed: Aug. 14, 2001

(86) PCT No.: PCT/AU01/00992

§ 371 (c)(1),
(2), (4) Date: Jul. 11, 2003

(87) PCT Pub. No.: WO02/13695

PCT Pub. Date: Feb. 21, 2002

(65) Prior Publication Data

US 2004/0015207 A1    Jan. 22, 2004

(30) Foreign Application Priority Data

Aug. 14, 2000 (AU) .................................. PQ9413

(51) Int. Cl.
*A61N 1/36* (2006.01)
(52) U.S. Cl. ...................................................... 607/48
(58) Field of Classification Search ................. 607/48, 607/49, 148
See application file for complete search history.

(56) References Cited

U.S. PATENT DOCUMENTS

| | | | |
|---|---|---|---|
| 3,769,636 A * | 11/1973 | Friedman | ...................... 623/24 |
| 4,421,336 A | 12/1983 | Petrofsky et al. | |
| 4,569,352 A | 2/1986 | Petrofsky et al. | |
| 4,697,808 A | 10/1987 | Larson et al. | |
| 4,724,842 A | 2/1988 | Charters | |
| 5,121,747 A * | 6/1992 | Andrews | ........................ 607/2 |
| 5,167,229 A * | 12/1992 | Peckham et al. | ............. 607/48 |

(Continued)

FOREIGN PATENT DOCUMENTS

EP    0 219 084 A2    4/1987

(Continued)

*Primary Examiner*—George R. Evanisko
*Assistant Examiner*—Michael Kahelin
(74) *Attorney, Agent, or Firm*—Finnegan Henderson Farabow GArrett & Dunner LLP

(57) ABSTRACT

A functional electrical stimulation system (30) for controlling the movement of a portion of a body of a subject (12), such as the subject's legs. The system (30) comprises a sensor (60) that in one arrangement is mountable to a portion of the subjects' body other than the legs, for example the torso (14). In another arrangement, the sensor (60) can be mountable to a walking aid, such as a crutch (20). The sensor (60) outputs signals representative of the position and/or movement of the torso (14) or walking aid (20). The system (30) also comprises a control means (32) that receives and processes the signals output by the sensor (60) and outputs control signals to a stimulator (35) adapted to provide electrical stimulation to the legs via electrodes (53) in response to the position and/or movement of the torso (14) or walking aid (20) as determined by the sensor (60).

3 Claims, 5 Drawing Sheets

U.S. PATENT DOCUMENTS 5,383,911 A    1/1995   Mann
5,662,693 A *  9/1997   Johnson et al. ............... 607/49

FOREIGN PATENT DOCUMENTS

| GB | 2302283    | 1/1997 |
| WO | WO 97/04705 | 2/1997 |
| WO | WO 97/10874 | 3/1997 |

* cited by examiner

INTERFACE TO FES CONTROL SYSTEM

FIELD OF THE INVENTION

The present invention relates to a functional electrical stimulation (FES) system and method of using such a system. More particularly, the invention relates to a device and method for providing a person using functional electrical stimulation with a means of controlling the electrical stimulation provided to their limbs.

BACKGROUND OF THE INVENTION

In the area of medical technology, much advancement have been made to assist individuals who have previously been considered to be disabled in some way, to lead a relatively normal life in spite of such disabilities. Such advancements include the provision of hearing aids and cochlear implants for the hearing impaired, as well as pacemakers for those who experience cardiac problems, to name a few. However with regard to persons suffering from spinal cord injury and those who have lost function of their limbs, the provision of a device or devices to return desired function to the individual has as yet proven difficult to implement. Functional electrical stimulation (FES) systems of various types are seen to have particular application in providing persons suffering from spinal cord injury or deficiency, such as paraplegia, with a capacity to make controlled movements of their dysfunctional legs.

Functional electrical stimulation systems use electronics to generate electrical impulses. These impulses are then delivered to the nerves or muscles of a subject via electrodes to stimulate movement of the muscles that are otherwise dysfunctional. In order for useful and controlled movements of limbs to be achieved several muscles must usually be operated in concert. This is normally achieved by an algorithm executed under the control of the FES system to deliver a pattern or sequence of stimulation impulses.

An important aspect of the successful implementation of such an FES system is the provision of a control technique that controls the limbs of a patient so that they follow a desired trajectory. It is extremely difficult, however, to choose a trajectory of the limbs so that a functional task such as standing is performed. In one proposal, control is provided by a touch pad interface which can be activated by the subject's fingers to some control types of movement, such as standing, sitting and walking.

Such touch pad interfaces as known in the art do not provide an intuitive interface for the subject with the FES system and assume that the subject has full hand control to enable use of such a device. Existing FES systems are, therefore, relatively difficult to learn how to use and require a certain amount of dexterity which has the potential to move subjects in undesirable ways.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of anti other element, integer or step, or group of elements, integers or steps.

According to a first aspect, the present invention is a functional electrical stimulation system for controlling the movement of a portion of a body of a subject comprising:

a measuring means having at least one sensor, mountable to a portion of the subject's body other said body portion, that outputs signals representative of the position and/or movement of said other portion of the subject's body; and a control means that receives and processes the signals output by the measuring means and outputs control signals to a stimulating means adapted to provide electrical stimulation to said body portion in response to the position and/or movement of said other body portion determined by the measuring means.

In one embodiment of this aspect, the said other body portion is selected from the group comprising the torso, the head or one or both arms of the subject.

In a further embodiment, said body portion is one or both legs of the subject.

The present invention provides a system that can be relatively easily used, in one arrangement, to generate one or more desired angles between the respective thighs and lower legs of a paraplegic with the legs being controlled by electrical stimulation of the muscles so that the actual measured angle of the thigh and lower leg corresponds to the desired angles.

In a preferred embodiment, the measuring means measures the angle of the subject's torso relative to a predetermined plane. The predetermined plane can be a sagittal plane, a frontal plane or a horizontal plane. In one embodiment, the measuring means only measures the angle when the torso has stopped gross movement. In another embodiment, the measuring means measures the angle throughout the range of movement of the torso.

In another embodiment, the measuring means detects torso movements that are determined by the control means as indicative that the subject wishes to roll over when they are in a horizontal position, such as when they are asleep. Such torso movements will typically comprise twisting movements of the torso.

In yet another embodiment, the measuring means measures the angle of the torso relative to the position of one or both of the lower limbs of the subject.

In one embodiment, the measuring means can be carried by the subject. The measuring means may be carried in a harness or clothing worn by the subject. In another embodiment, the measuring means may be strapped about the torso of the subject. In an alternative embodiment, the measuring means or componentry thereof can be implantable within the subject.

In a preferred embodiment, the measuring means comprises one or more transducers that outputs signals representative of the position and/or movement of the transducer to the control means. Where the measuring means is measuring the angle of the torso relative to the lower limbs, a transducer can be mounted on the torso and on one or both of the lower limbs. More than one transducer mounted on the torso and/or the lower limbs can be envisaged. Each of the transducers in this case would output signals to the control means.

The control means preferably processes the output signals of the transducer or transducers and then outputs signals to the stimulating means to provide electrical stimulation to the muscles of the subject. The control means can execute an algorithm that leads to provision of electrical stimulation to the appropriate muscle(s) at the appropriate intensity as dictated by the subject or a predetermined programme. The output signals of the transducer or transducers and those of the control means to the stimulating means can comprise electrical or optical signals.

In a further embodiment, the control means can have a storage means having at least one predetermined action sequence storable therein. On receipt of signals from the measuring means, said at least one predetermined action sequence can be provided to the stimulating means. The predetermined action sequence can result in the subject moving from a standing to a sitting position, or moving from a sitting to a standing position, walking, or moving the legs in a pedalling action. Other suitable predetermined action sequences can be envisaged.

In one embodiment, the control means is adapted to output a predetermined sequence of signals to the stimulating means upon receiving signals from the transducer or transducers that the subject's torso is at a particular pre-determined angle relative to a plane, such as a notional horizontal plane, or the lower limbs. For example, when the subject bends their torso forward from the hip this can be measured by the transducer with appropriate signals provided to the control means.

In one embodiment, the pre-determined sequence of signals to the stimulating means can be output by the control means when the torso has bent forward by an angle of between about 10° and about 60°, more preferably between about 25° and 50°, and still more preferably between about 25° and 45°.

In another embodiment, the control means is adapted to output a series of pre-determined signals representative of the position of the subject's torso. A particular series of various positions of the torso can cause the control means to output a particular series of signals to the stimulating means so causing a particular series of stimulations to the muscles of the subject. This allows a subject to learn a particular series of movements that lead to a particular desired series of movements of the stimulated limbs of the subject. For example, a movement or series of movements of the torso may initiate a step by a leg or a series of steps by the subject's legs. Alternatively, a movement or a series of movements of the torso may initiate ate a standing or sitting action.

In response to the detection of signals from the control means, the stimulating means is adapted to output electrical impulses. These impulses are transmitted to the subject's nerves or muscles from a stimulator through electrically conducting leads to stimulation electrodes. The electrodes can be surface mounted on the skin of the subject, percutaneous intramuscular electrodes that are implanted with a minimally invasive needle insertion procedure, or fully implanted electrodes. The stimulating means preferably has circuitry adapted to drive whatever electrodes are selected for use with a particular subject.

In one embodiment, the stimulator can be carried by the subject. The stimulator can be carried in a harness or clothing worn by the subject. In another embodiment, the stimulator may be strapped to the subject. In an alternative embodiment, the stimulator or componentry thereof can be implanted within the subject. The electrical leads extending from the stimulator to the electrodes can be totally implantable within the subject or carried externally on the body of the subject.

In a preferred embodiment, the electrodes can be mounted to the lower limbs of the subject. It will be envisaged that the electrodes could be mounted to the upper limbs or that electrodes may be mounted to both the upper and lower limbs of the subject.

Where the electrodes are mounted to the lower limbs, the predetermined sequence of signals generated by the control means is provided to the lower limbs.

In the embodiment where a bend of the torso to a pre-determined angle relative to the horizontal plane is made, the control means can be programmed such that the predetermined sequence of signals generated on detection of such a change in the position of the torso causes the subject to be moved from a sitting position to a standing position or vice versa.

As discussed above, in another embodiment, a particular series of various positions of the torso can cause the control means to output a particular series of signals to the stimulating means so causing a particular series of stimulations to the muscles of the subject. For example, when the subject is in a particular pre-determined position, the angle of the torso relative to the horizontal plane can determine the angle between the thigh and lower leg of each leg of the subject. The control means preferably only allows torso movement to control limb angle when the subject is in a position that variation in limb angle is appropriate or safe for the subject. When the torso is upright, the angle between the torso and the horizontal plane is about 90°. If the angle between the thigh and lower leg is not about 90°, the stimulating means stimulates the muscles within the leg until this angle is achieved. This should be relatively comfortable for the subject as when sitting upright in a chair a person's thighs are typically about normal to the lower leg. When the subject bends their torso relatively forward, the angle between the torso and the horizontal plane decreases. This decrease in angle leads the control means to output signals causing flexion of the lower leg, preferably to a predetermined degree, so moving the feet to a position ready to allow the subject to stand. Once the feet se in position, the subject can, for example, move their torso backwardly relative to the horizontal plane. This movement, if detected by the control means following the previous forward movement, can lead the control means to cause full extension of the legs so moving the subject from a sitting to standing position.

Detection of other movements of the torso can lead the control means to output other pre-programmed sequences of signals. For example, if the subject considers that they are not in a position to stand once the feet have been moved the predetermined degree, a her forward or other movement of the torso can cause the control means to stimulate the lower leg to return to a position about 90° relative to the thigh so leaving the subject in a sitting position.

When a subject is in a standing position, controlled movement of the torso can allow the subject to move to a sitting position. For example, forward bending of the torso relative to the horizontal plane (so decreasing the angle of the torso to the notional horizontal plane) can cause the control means to stimulate the legs of the subject to decrease the angle between the thigh and lower leg from about 180° gradually towards about 90° at which point the legs are in a position to allow the subject to comfortable sit upon a chair.

In another embodiment; when the subject is in a particular predetermined position, variation in the angle of the torso and/or head, or both in combination, relative to the lower limbs can allow a subject to control initiation of a step or sequence of steps. Sequential variations in torso position relative to the lower limbs can control a series of alternate steps by the subject's legs. Preferably, the subject can learn to perform this sequential variation in torso and/or bead angle and so control their step movement. Again, the control means preferably only allows torso movement to control step initiation when the subject is in a position that step initiation is appropriate or safe for the subject.

A system of using torso and/or head angle allows the subject to define their preferred limb angle. This allows the subject to be trained to control the standing and sitting process or walking using the FES system. This gives the subject a greater sense of controlling the stimulation provided to their limbs rather than being in a position of feeling that the system is entirely in control of their movement. This is envisaged as providing the subject with a greater sense of confidence in using function electrical stimulation systems so leading to greater use of the system.

As discussed above, the control means can be adapted to output a predetermined sequence of signals to the stimulating means on receiving signals from the transducer that the subject is twisting their torso in a manner indicative that the subject wishes to roll over. In this case, the stimulating means can be adapted to stimulate the legs in a manner that assists the subject in turning over. In one embodiment, the system will assist turning over when the subject is asleep. In his case, it is preferred that the stimulations to the legs are just sufficient to assist turnover without being of a magnitude that significantly disturbs the sleep of the subject.

In a preferred embodiment, stimulation of the legs to assist turning over is only activated by the control means when the patient is lying in a substantially horizontal plane. For example, the transducer can determine the orientation of the subject and provide a signal to the control means representative of the orientation. In such instances, whenever the transducer is outputting a signal that indicates that the subject is not substantially horizontal, the control means is locked from outputting the signal sequence that would be employed to assist rolling over.

In another embodiment, the control means can be programmed to output signals to the stimulating means to cause roll over of the subject at predetermined times or at predetermined rates. For example, the control means can be programmed to output signals causing roll over of the subject at least 2 times in an 8 hour period. These roll overs could be additional to those that occur in response to detection of torso twisting or movement indicating a desire by the subject to roll over. In one embodiment, the control means could monitor the number of assisted roll overs performed in response to torso movement or twisting and only institute an involuntary roll over if the subject has not rolled over for a predetermined minimum period of time. For example, the control means may be adapted to institute an involuntary roll over if no roll over has occurred for at least 4 hours.

Assistance in rolling over provided by the present system should reduce the incidence of pressure sores and disrupted sleep for spinal cord injured persons who are unable to relieve pressure during sleep by rolling over.

In a preferred embodiment, the system includes a feedback means that measures the position and/or movement of said body portion being stimulated by the stimulating means and provides output signals to the control means representative of these measurements. The feedback means can comprise one or more transducers mounted to the limbs being stimulated. Where a subject's legs are being stimulated, one or more transducers may be mounted to the thigh and/or lower leg of the subject. In another embodiment, the transducers can be fully implantable within the legs.

The signals provided by the feedback means can be used to override the instruction provided by the subject by bending their said other body portion, such as their torso, if the control means detects that the limbs are in an unsuitable position to be stimulated. Once stimulation has commenced, for example to cause the subject to stand, the control means can also use the output signals of the feedback means to determine if the limbs of the subject are responding and to adjust the pattern and location of the stimulation if required. Such a feedback means provides the system with the flexibility to adjust its performance depending on the circumstances faced by the subject. For example, a different stimulation pattern may be required to successfully move a subject from a sitting position on a low couch to a standing position compared to that required to achieve the same result from sitting in an upright chair.

The signals provided by the feedback means can also be used by the control means as a means of determining if the subject is in a substantially horizontal position. If the feedback means outputs signals to the control means that the subject is not substantially horizontal, the control means is preferably locked from outputting the sequence of signals that would normally be output to the stimulating means to assist rolling over on detection of torso movements normally indicative that the subject does wish to roll over.

In a preferred embodiment, the control means has an operating means. The operating means preferably comprises an activation and deactivation means. The activation and deactivation means preferably allows the subject to turn on and off the control means and the FES system when desired. Where the FES system is fully implanted, the activation and deactivation means is preferably controllable from outside the body. In one embodiment, the activation and deactivation means can comprise a switch. Where the control means is implanted, the system preferably can still be operated through the skin of the subject. The operating means preferably incorporates a locking means to prevent inadvertent activation or deactivation.

Where implanted, an external controller can communicate with the implanted unit using radio frequency (RF) transmissions.

According to a further aspect, the present invention is a functional electrical stimulation system for controlling the movement of a portion of a body of a subject comprising:

a measuring means having at least one sensor, mountable to a walking aid, that outputs signals representative of the position and/or movement of said walking aid when operated by a subject of the system; and a control means that receives and processes the signals output by the measuring means and outputs control signals to a stimulating means adapted to provide electrical stimulation to said body portion in response to the position and/or movement of said walking aid determined by the measuring means.

In this aspect, the subject can learn a series of positions and/or movements of the aid that cause pre-programmed control signals or sequences thereof to be supplied to the stimulating means.

In one embodiment, the walling aid can comprise a crutch or walking sticks. Placement of the crutch or stick at a particular angle relative to vertical or its movement in a particular way can be pre-programmed to cause stimulation of a lower limb in a manner that allows the subject to walk. In a preferred embodiment, the system relies on at least one measuring means mounted on respective crutches supporting the subject. A particular movement or position of the left crutch can be adapted to cause stimulation of the right leg. A subsequent particular movement or position of the right crutch can be adapted to cause stimulation of the left leg. In this manner, a subject can learn to walk using the FES system by alternately moving or adjusting the position of the crutches used to support them. In an alternative arrangement, it can be envisaged that the subject rely on one crutch or walking stick. In this case, variation in the position and/or movement of the aid can lead to stimulation of the opposing leg. The adjacent leg can then be stimulated to take a stride 180° out of phase of the opposing leg.

In this aspect, the monitoring means, control means and stimulating means can have the features of the equivalent systems already defined herein.

According to a still further aspect, the present invention is a walking aid for a subject being assisted to walk using functional electrical stimulation system, the walking aid having at least one sensor mounted thereon that outputs signals representative of the position and/or movement of the walking aid.

In this aspect, the functional electrical stimulation system can have the features of the FES system defined above.

In this aspect, the walking aid can comprise a crutch. The crutch can comprise a tall crutch that fits under the armpits with double uprights and a small horizontal band bar extending between the uprights, a Lofstrand crutch which consists of a single tube of aluminum surrounded by a metal cuff that fits round the forearm and has a handbar positioned proximally thereto, or a Canadian elbow extensor crutch which is a variation of the Lofstrand crutch. Still further, the walking aid can comprise a walked stick.

The walking aid can have an on-board power supply, such as a rechargeable battery, that provides power to the sensor. In another embodiment, componentry of the FES system, such as the control means and stimulator can be mounted on or in the walking aid. Electrical connectors can also be incorporated into the walking aid to allow cables to extend from the componentry mounted to or in the walking aid to the one or more transducers and/or the stimulating electrodes.

According to a further aspect, the invention is a method of controlling functional electrical stimulation provided to a portion of a body of a subject, the method comprising the steps of:

measuring the position and/or movement of a portion of the body of the subject other than said body portion; and processing the signals and outputting electrically stimulation to said body portion in response to the measured position and/or movement of said other body portion.

In a preferred embodiment of this aspect, the method is adapted to use the position and/or movement of the torso, the head, one or both arms, or a combination thereof, to control the stimulation provided to the legs of the subject. In a particularly preferred embodiment, the position and/or movement of the torso and/or head can be used to initiate and control a standing or sitting action of the subject. In another embodiment, the movement of the torso and/or head can be used to initiate stimulation of the legs that allows the subject to roll over when in a substantially horizontal position.

According to a still further aspect, the invention is a method of controlling functional electrical stimulation provided to a port on of a body of a subject, the method comprising the steps of measuring the position and/or movement of a walking aid operated by the subject; and processing the signals and outputting electrical stimulation to said body portion in response to the measured position and/or movement of said walking aid.

In a preferred embodiment of this aspect, the electrical stimulation is provided to the legs of the subject to cause the subject to walk.

In a preferred embodiment of these latter aspects, the method includes a step of measuring the position and/or movement of the legs and using the measurements to modify or control the electrical stimulation generated in response to movement of the subjects torso or walking aid.

BRIEF DESCRIPTION OF THE DRAWINGS

By way of example only, preferred embodiments of the invention are now described with reference to the accompanying drawing, in which.

PREFERRED MODE OF CARVING OUT THE INVENTION

Figure 5:
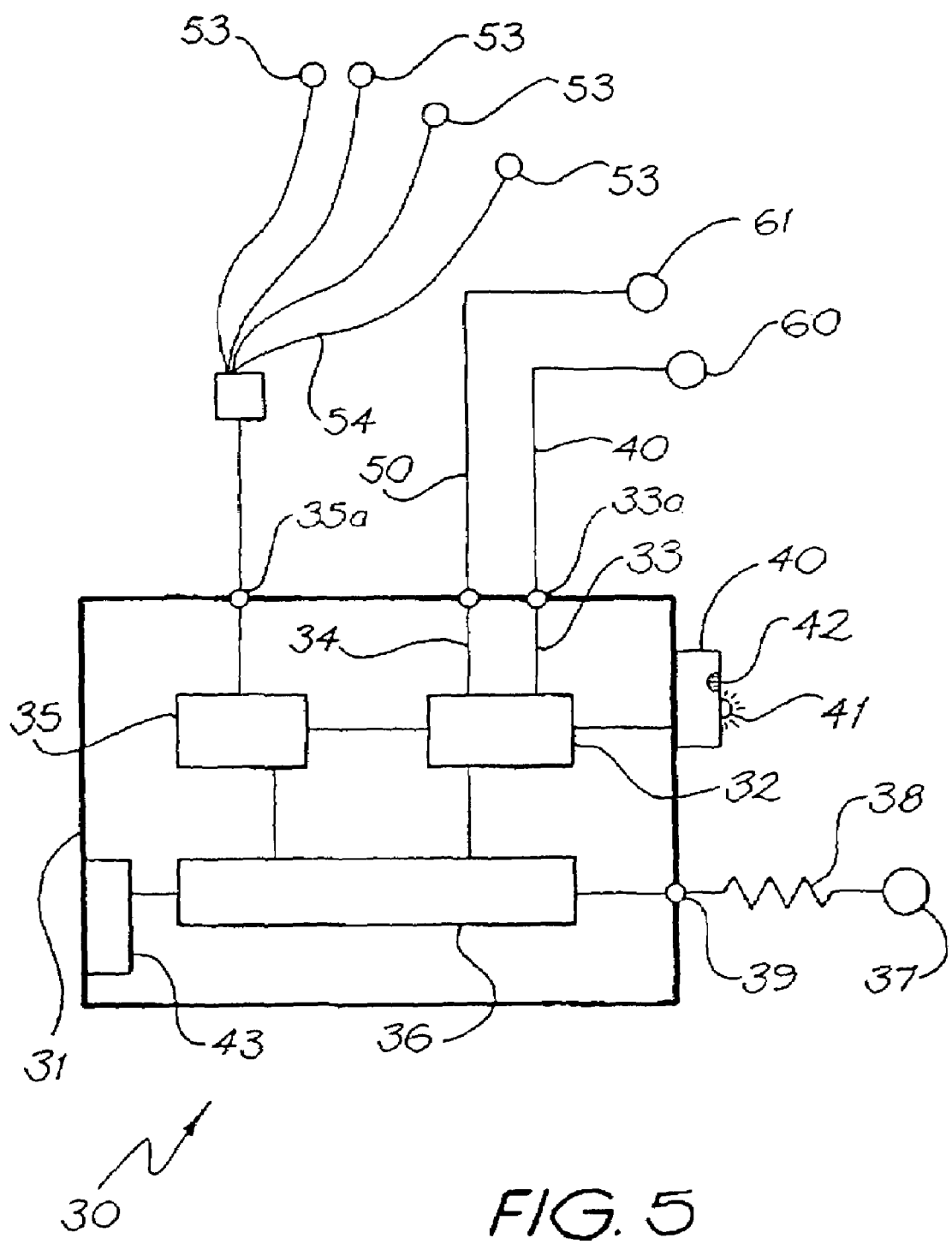
FIG. 5 is a simplified block diagram depicting one embodiment of a FES system according to the present invention.

A FES system according to the present invention is generally depicted as 30 in FIG. 5.

The system has a housing 31 that houses a control means 32 and a stimulator 35. A power source in the form of a rechargeable battery 43 is also provided in the housing 31. The depicted control means 32 receives a first set of signals through a first signal path 33 provided by a cable 40 extending from a first transducer 60 to an electrical connector 33a on the housing 31. The transducer 60 and cable 40 are depicted schematically in FIG. 5 and are not shown to scale. The transducer 60 is adapted to be mounted to a portion of the body of the subject that is under the control of the subject. For example, in the case of subject with paraplegia, the transducer can be mounted to the upper torso of the subject.

The signals output by transducer 60 and provided through signal path 33 represent the magnitude and type of movement of the torso made by the subject.

While the control means 32 could rely only on the input from transducer 60, the depicted control means 32 also receives a second set of output signals through a second signal path 34 provided by a cable 50 extending from a transducer 61. Transducer 61 can also be mounted to the torso of the subject or at another location on the subjects body. While depicted schematically in FIG. 5, the cables 40,50 can be envisaged as being a flexible cables extending between the respective transducers 60,61 and the connectors 33a,34a of the housing 31. The signals output by transducer 61 and provided through signal path 34 can also represent the magnitude and type of movement made by the portion of the subject's body to which the transducer 61 is mounted.

In one arrangement the control means 32 receives the first set of output signals through the first signal path 13 from transducer 60 when mounted to the torso of the subject and the second set of output signals through the second signal path 34 from transducer 61 mounted to one of the legs of the subject. While FIG. 5 depicts only one transducer providing signals through each of the signal paths 33 and 34, more than one transducer could be utilised to provide signals through each signal path.

The transducer 60 mounted to the torso of the subject 12 provides a signal output representative of the angle of the torso relative to a horizontal plane and the movement of the torso. The transducer 61 mounted to one of the legs of the subject provides a signal output representative of the angle of the thigh of the leg relative to a horizontal plane and the movement of the legs. When monitoring only one leg, the control means 32 can be operated in a manner that assumes the other leg is in a position 180° out of phase to the monitored leg, when the subject is receiving functional electrical stimulation that results in the subject being able to walk or move their legs in some repetitive manner, such as rotate the pedals of an exercise bicycle.

FIG. 1 depicts one use of one embodiment of the FES system 30 depicted in FIG. 5. In FIG. 1, a simplified view of a subject 12 receiving functional electrical stimulation is depicted. In FIG. 1a, the subject 12 is shown seated on a chair 13. As shown in FIG. 1b, the subject 12 can move their torso 14 forwardly to a position that is at a particular angle relative to a horizontal plane. The transducer 60 mounted to the torso 14 detects this movement and outputs signals representative of this to the control means 32. The control means 32 on receipt of these signals in turn outputs suitable control signals to the stimulator 35 which outputs electrical impulses to electrodes 53 mounted to the legs 15 of the subject 12. For reasons of clarity, the system 30 and electrodes 53 are not depicted in FIG. 1

Figure 1A:
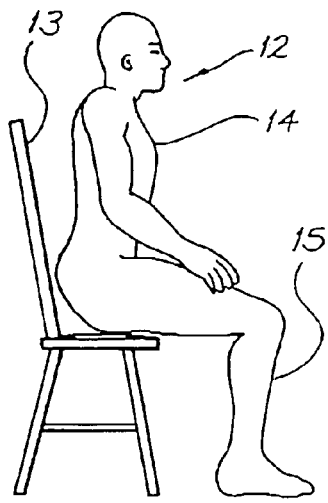
FIG. 1 is a sequence of drawings depicting the movement of a subject's body from a sitting position to a standing position using functional electrical stimulation.
Figure 1B:
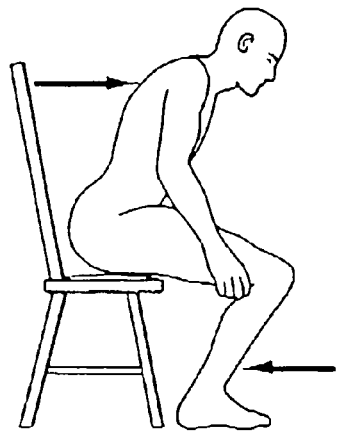

As can be seen in FIG. 1b, as the subject 12 moves their torso 14 forward, the lower legs of the subject 12 move backwardly. The angle of the torso 14 controls the angle of movement of the lower legs about the knees of the subject 12.

Figure 1C:
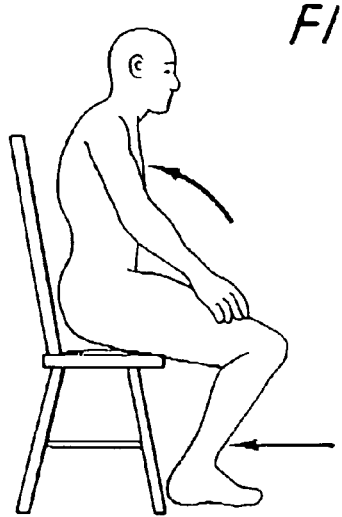
Figure 1D:
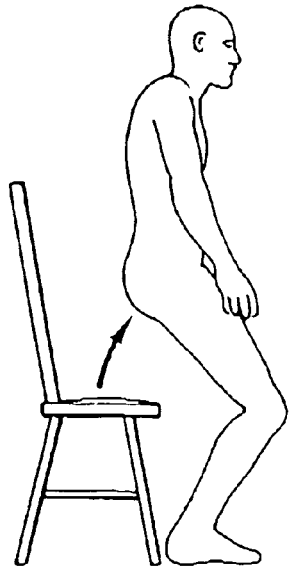
Figure 1E:
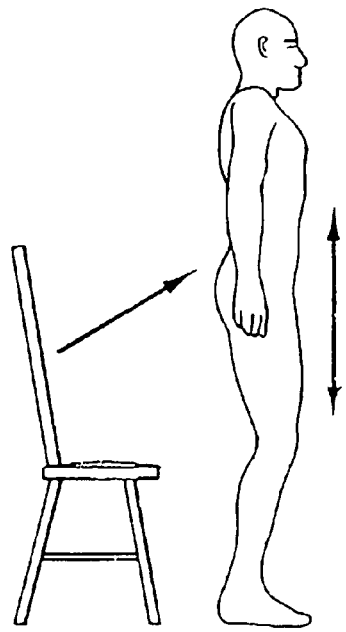

Once the feet of the subject 12 are in the correct position, the subject 12 can return their torso 14 back to an upright position as depicted in FIG. 1c. This movement leads to further signals being output to the control means 32. Once the torso 14 is back in an upright position, the control means 32 can output control signals to the stimulator 15 which result in the stimulator 35 outputting a sequence of stimulation impulses to the legs 15 that result in the subject 12 moving to a standing position (see FIGS. 1d and 1e).

Figure 2C:
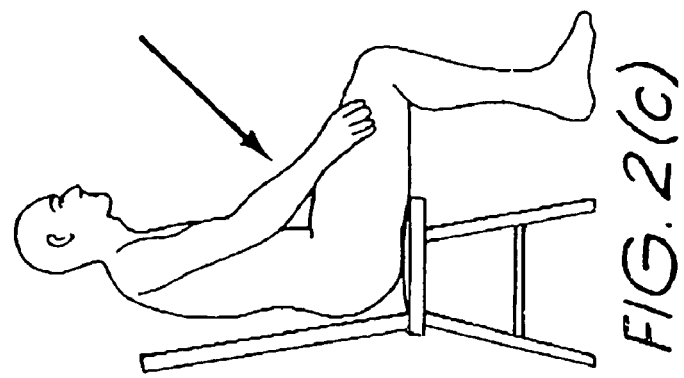
FIG. 2 is a sequence of drawings depicting the movement of a subject's body from as standing position to a sitting position using functional electrical stimulation.
Figure 2B:
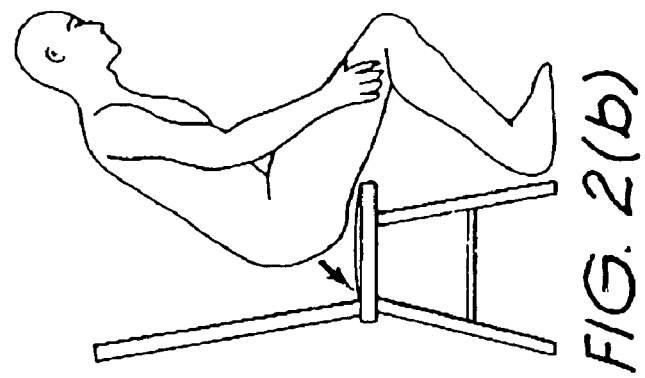
Figure 2A:
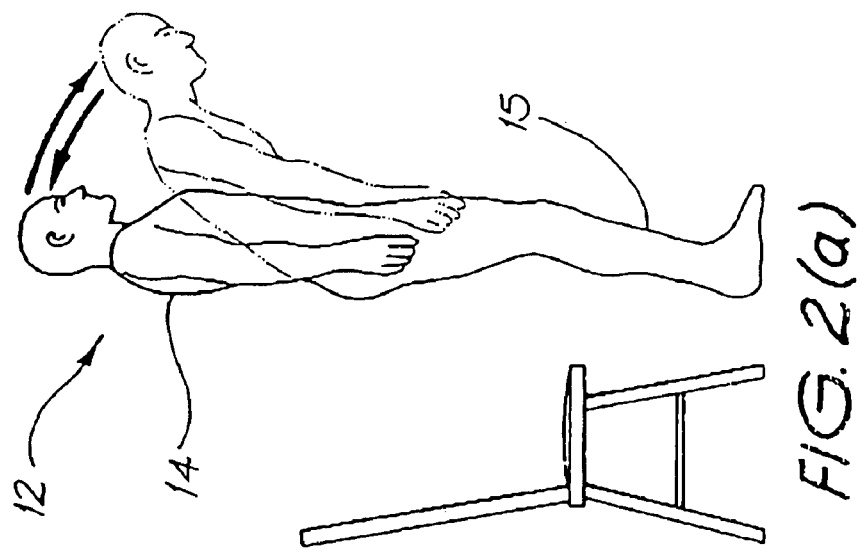

FIG. 2 depicts another use of an embodiment of the FES system 30. In these figures, the subject 12 is firstly shown standing in front of a chair 13. On a subject 12 moving their torso 14 forward a particular desired angle, such as greater than 30°, and then returning to an upright position within a predetermined time (see FIG. 2a), the transducer 60 detects this combination of movements and outputs appropriate representative signals to the control means 32. The control means 32 on receiving this combination of signals, outputs control signals to the stimulator 35 which results in the thighs of the subject 12 bending backwardly relative to the knees (see FIG. 2b) so as to move the subject 12 back down onto the chair 13 as depicted in FIG. 2c.

FIGS. 1 and 2 depict examples of how the FES system 30 can be used by the subject 12 adjusting their torso to control the movement of their dysfunctional legs.

The control means 32 is programmed to output a particular stimulation signal sequence to the stimulator 35 on detection of a predetermined torso position adopted by the subject 12. In this way, the subject 12 can learn to create particular different stimulation patterns or signal sequences by the stimulator 35 by adopting various different torso positions.

While the use of torso orientation is depicted in FIGS. 1 and 2 for initiating a standing up or sitting down action, torso orientation changes can also be used to initiate and maintain a walling sequence. In another embodiment, the control means 32 can be adapted to watch for twisting movements of the torso that are indicative, when the subject is laying down, that the subject wishes to roll over. The control means can also include a timer means that ensures the subject 12 rolls over a predetermined number of times in a particular time period.

The transducer 61 mounted to the legs of the subject 12 can also be utilised as a means of feeding back information to the control means 32 following electrical stimulation of the legs by the stimulator 35. For example, the transducer 61 can inform the control means 32 that the stimulator 35 has or has not achieved the outcome for the legs expected by the provided stimulation.

The control means 32 can also control the stimulation applied by the stimulator 35 based on a comparison of angles or orientation of the torso relative to the upper and lower leg (knee) angle. As previously mentioned, the detected torso angle relative to the horizontal plane can be approximated to the desired knee angle such that the desired knee angle can be considered as a function of the measured torso angle. The control means 32 can then initiate appropriate signals to ensure that the actual knee angle closely approximates that of the desired knee angle based on a model of desired knee angles and torso angles.

The depicted control means 32 comprises a microprocessor and includes a data storage buffer that stores measured torso movements measured by the transducer 60 and/or leg movements resulting from the provision of electrical stimulation thereto.

Figure 3:
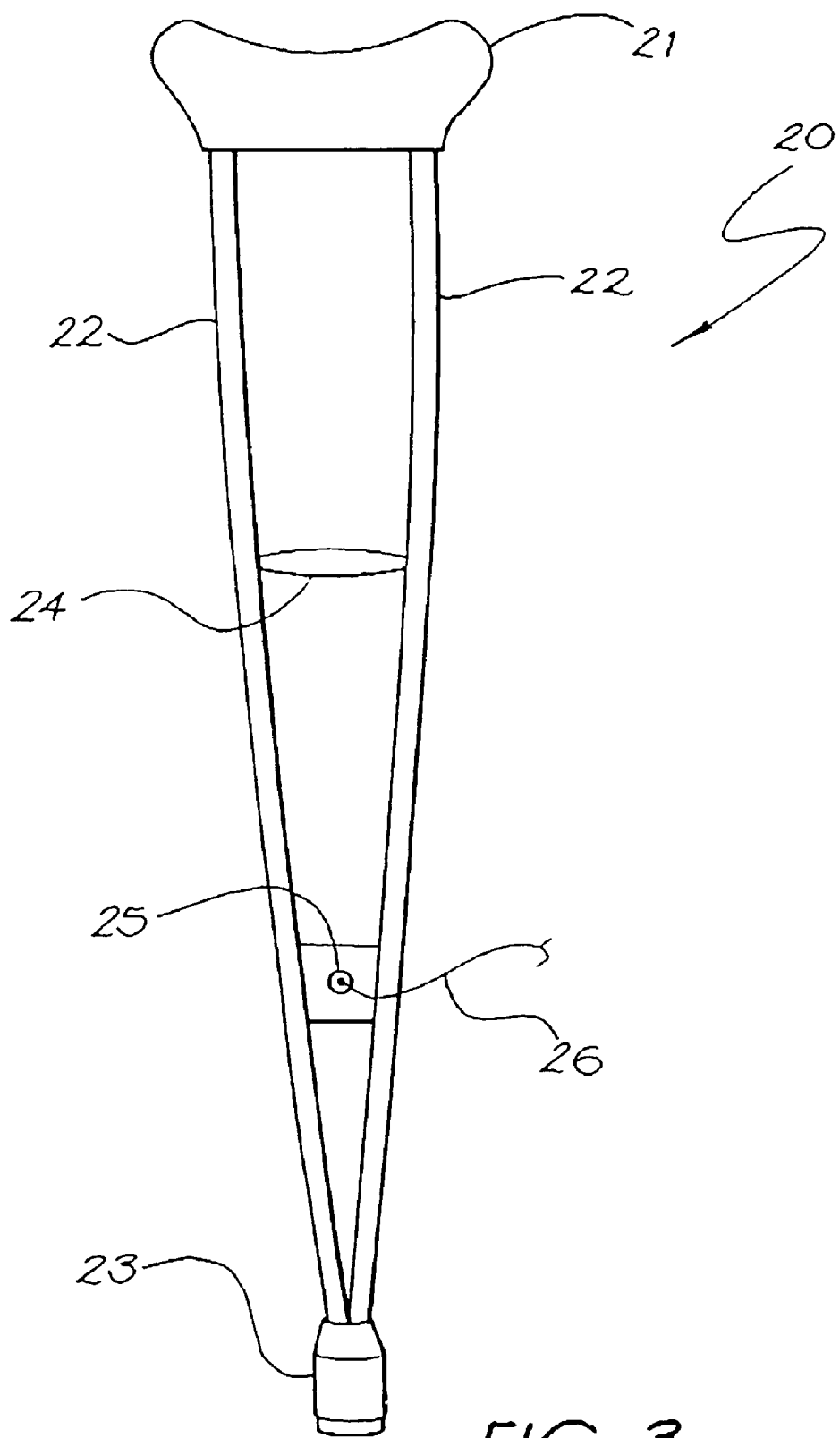
FIG. 3 is a side elevation view of one embodiment of a walking aid according to the present invention.

One embodiment of a crutch for use as a walking aid according to the present invention is depicted generally as 20 in FIG. 3. The depicted crutch 20 comprises a standard tall crutch, however, the present invention could also equally rely on a Lofstrand crutch or Canadian elbow extensor crutch.

The crutch 20 has an armpit portion 21 and two double uprights 22 that extend from the armpit portion 21 to a foot 23. A small horizontal handbar 24 extends between the uprights 22 which allows the subject 12 to use and support themselves on the crutch 20.

Mounted to the crutch 20 below the handbar 24 is a transducer 25. The transducer 25 can have the same or different features to that of transducer 60 described above. Extending from the transducer is a cable 26. In the depicted embodiment, cable 26 is adapted to be electrically connected to connector 33a of the FES system 30. The transducer 25 is used to provide signals to the control means 32 in replacement of or in addition to signals provided by transducer 60 mounted to the torso of the subject 12. By varying the position of one or two crutches being used by the subject 12, the subject 12 can control the stimulation pattern output by the stimulator 35. In one example, forward movement of the left crutch can result in a forward step of the right leg of the subject 12 and subsequent forward movement of the right crutch can result in a forward step of the left leg of the subject 12. Further the control means 32 of this embodiment can determine the distance between the subject's leg and the associated crutch and cause the leg to be brought towards the crutch when the distance exceeds a specific limit. By learning to appropriately move the supporting crutches, a subject 12 can create a sequence of steps using the FES system 30.

While FIG. 3 only depicts the transducer 25 mounted to the crutch 20, in another embodiment, the housing 31 could be mounted on the crutch 20.

Figure 4C:
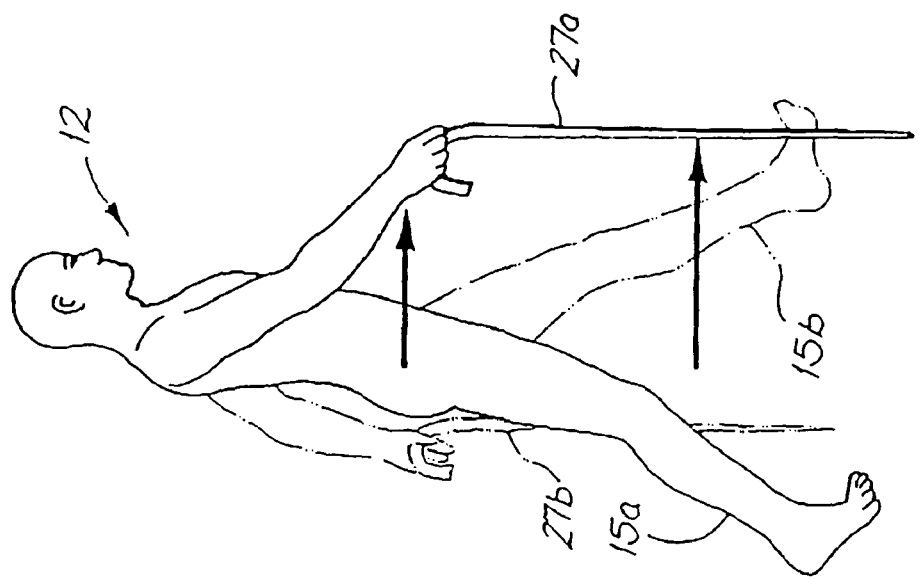
FIG. 4 is a sequence of drawings depicting the gait of a person using walking aids in concert with a functional electrical stimulation system.
Figure 4B:
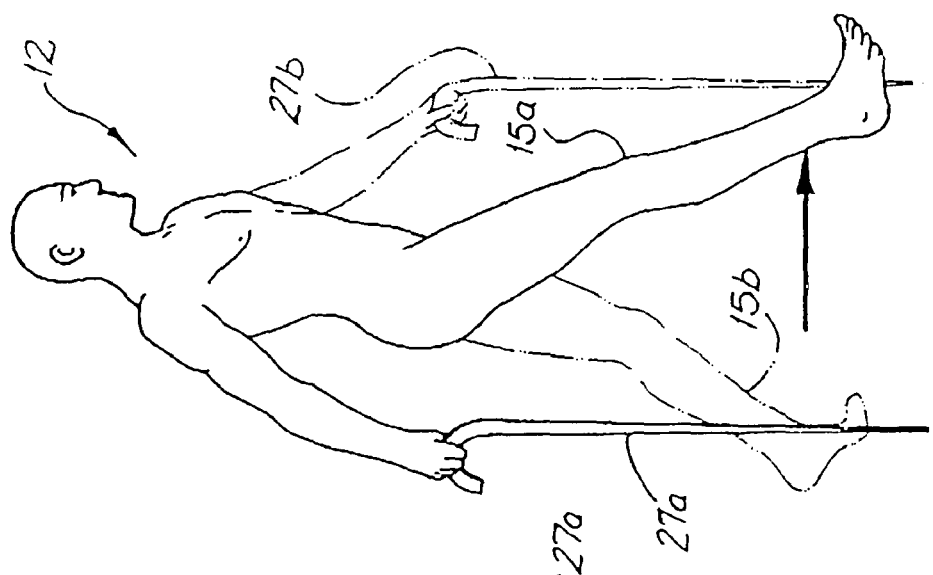
Figure 4A:
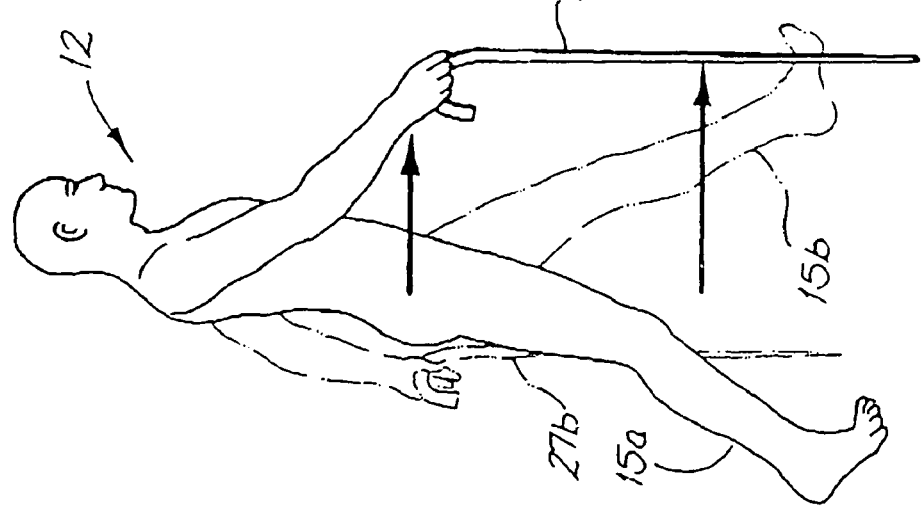

FIG. 4 depicts a subject 12 using a walking stick in each hand to control the FES system 30 in a manner similar to that described for crutch 20. Walking stick 27a is in the right hand of the subject 12 and walking stick 27b in the left band. For the purposes of clarity, the left leg, left arm and left walking stick 27b of the subject 12 are depicted in phantom in FIG. 4.

Each walking stick 27a,27b has a transducer 25 mounted thereon (not visible) that is used to provide signals to the control means 32 in replacement of or in addition to signals provided by transducer 60 mounted to the torso of the subject 12. By varying the position of the sticks 27a,27b, the subject 12 can control the stimulation pattern output by the stimulator 35.

In one example, forward movement of the left stick 27b can result in a forward step of the right leg 15a of the subject 12 and subsequent forward movement of the right stick 27a can result in a forward step of the left leg 15b of the subject 12. As depicted in FIG. 4b, the subject 12 has moved the left stick 27b forward which in turn has resulted in the subjects right leg 15a stepping forward a distance similar to or the same as that moved by the left stick 27b. Once this step is complete, the subject 12 can move the right stick 27a forward (as depicted in FIG. 4c) which in turn leads the FES system 30 to move the left leg 15b forward a distance similar to or the same as that moved by the right stick 27a. By continuously moving the sticks 27a,27b forward in alternate fashion, the subject 12 can walk across a surface.

While the use of the sticks 27a,27b is depicted in FIG. 4 as resulting in a walking movement of the subject 12, it will be appreciated that other movements of one or both sticks can result in other movements of the subject 12. For example, the lifting of one of the sticks may cause the subject to sit or stand.

The components of the depicted FES system 30 can be fully implanted within the subject 12. It will, however, be appreciated that the control means 32 and other components could be external the body of the subject 12. Electrical stimulation to the muscles is provided, in the depicted embodiment, by electrodes 53 mounted to the skin or implanted within the muscles identified as requiring stimulation to achieve the movement desired when installing the system 30. As depicted in FIG. 5, the electrodes 53 are electrically connected by cables 54 to the output of stimulator 35 through a connector 35a on the housing 31.

As depicted in FIG. 5, the system 30 further comprises an operating means 36 that receives signals from a transducer 37 adapted to monitor the position of another portion of the subjects body, such as the subject's head. The transducer 37 outputs signals through cable 38 connected to connector 39 in the housing 31. The transducer 37 and cable 38 are not depicted to scale. More than one such transducer 37 can also be envisaged. On receipt of a predetermined signal from the transducer 37, the operating means can activate or deactivate the control means 32 and/or the stimulator 35. For example, the transducer 37 can be mounted to the head of the person 12, and adapted to output a predetermined signal on determination of a particular movement of the person's head relative to the their torso. This provides the person 12 with a ready means to activate or deactivate the FES system 30 simply by a predetermined movement of their head. It can be envisaged that movement of the subject's torso 14 or the walking aid 20 held by the person 12 could also be used to activate or deactivate the control means 32 and/or the FES system 30.

The FES system 30 provides a relatively easier and more natural interface for the subject 12 to initiate a step or other movement when compared to button presses using known touch pad interfaces.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A functional electrical stimulation system for controlling the movement of a portion of a body of a subject comprising:
    a measuring device having at least one sensor that is mountable to the torso of the subject and which outputs signals representative of the angle of said subject's torso relative to a predetermined spatial reference plane;
    a controller that receives and processes the signals output by the measuring device and outputs control signals; and
    a stimulator that receives the control signals and is adapted to provide electrical stimulation to said one or both legs in response to the angle of the subject's torso determined by the measuring device;
    wherein, on detecting twisting movements of the torso and that the subject is at least substantially horizontal, the controller outputs control signals that cause the stimulator to output a sequence of stimulation impulses that serve to roll the subject over.

2. The function electrical stimulation system of claim 1 wherein the controller is programmed to output signals to the stimulator to cause roll over of the subject at predetermined times.

3. The functional electrical stimulation system of claim 2 wherein the controller is programmed to output signals causing roll over of the subject at least 2 times in an 8 hour period.

* * * * *